(12) United States Patent
Takikawa

(10) Patent No.: US 11,723,717 B2
(45) Date of Patent: Aug. 15, 2023

(54) HIGH-FREQUENCY FORCEPS

(71) Applicant: RIVERFIELD INC., Tokyo (JP)

(72) Inventor: Kyohei Takikawa, Tokyo (JP)

(73) Assignee: RIVERFIELD INC., Tokyo (JP)

( * ) Notice: Subject to any disclaimer, the term of this patent is extended or adjusted under 35 U.S.C. 154(b) by 0 days.

(21) Appl. No.: 17/592,867

(22) Filed: Feb. 4, 2022

(65) Prior Publication Data

US 2022/0151686 A1 May 19, 2022

Related U.S. Application Data

(63) Continuation of application No. PCT/JP2020/020727, filed on May 26, 2020.

(30) Foreign Application Priority Data

Aug. 8, 2019 (JP) ................. 2019-146416

(51) Int. Cl.
*A61B 18/14* (2006.01)
*A61B 18/12* (2006.01)
*A61B 18/00* (2006.01)

(52) U.S. Cl.
CPC ...... *A61B 18/1445* (2013.01); *A61B 18/1206* (2013.01); *A61B 2018/00059* (2013.01);
(Continued)

(58) Field of Classification Search
CPC ............ A61B 18/1445; A61B 18/1206; A61B 2018/00059; A61B 2018/00077; A61B 2018/00083; A61B 2018/1253
See application file for complete search history.

(56) References Cited

U.S. PATENT DOCUMENTS 5,766,167 A * 6/1998 Eggers ............... A61B 18/1445
 606/42
5,769,841 A 6/1998 Odell et al.
(Continued)

FOREIGN PATENT DOCUMENTS

CN 104144654 A 11/2014
CN 208464030 U 2/2019
(Continued)

OTHER PUBLICATIONS

International Search Report for PCT/JP2020/020727 dated Aug. 25, 2020 [PCT/ISA/210].
(Continued)

*Primary Examiner* — Joanne M Rodden
*Assistant Examiner* — Sean W Collins
(74) *Attorney, Agent, or Firm* — Sughrue Mion, PLLC

(57) ABSTRACT

High-frequency forceps for medical use that include a manipulation part including a grasping portion that is conductive; a cylindrical part that is inflexible, through which a wire for manipulation of the grasping portion and a cable for supplying current to the grasping portion are guided; and an insulating part that electrically insulates the manipulation part from the cylindrical part. The cylindrical part includes: an outer layer made of an insulating material; an inner layer made of an insulating material; and an intermediate layer located between the outer layer and the inner layer, and having a lower insulation resistance and a higher stiffness than the outer layer and the inner layer.

15 Claims, 2 Drawing Sheets

(52) U.S. Cl.
CPC ............. *A61B 2018/00077* (2013.01); *A61B 2018/00083* (2013.01); *A61B 2018/1253* (2013.01)

(56) References Cited

U.S. PATENT DOCUMENTS

| | | | |
|---|---|---|---|
| 2007/0106295 A1* | 5/2007 | Garrison | A61B 18/1445 606/50 |
| 2008/0009857 A1* | 1/2008 | Yanuma | A61B 18/1445 606/46 |
| 2009/0216248 A1* | 8/2009 | Uenohara | A61B 17/29 606/130 |
| 2010/0042097 A1 | 2/2010 | Newton et al. | |
| 2011/0251608 A1* | 10/2011 | Timm | A61B 18/1445 606/208 |
| 2014/0350540 A1* | 11/2014 | Kitagawa | A61B 18/1445 606/34 |
| 2016/0193001 A1* | 7/2016 | Lee | A61B 34/71 606/130 |
| 2016/0367279 A1 | 12/2016 | Orphanos et al. | |
| 2017/0119458 A1* | 5/2017 | Gudeman | A61B 18/1445 |
| 2020/0000512 A1* | 1/2020 | Heiliger | A61B 17/295 |

FOREIGN PATENT DOCUMENTS

| | | |
|---|---|---|
| JP | 11-155876 A | 6/1999 |
| JP | 2002-505139 A | 2/2002 |
| JP | 2009-202001 A | 9/2009 |
| JP | 2018-099401 A | 6/2018 |
| WO | 99/44523 A1 | 9/1999 |

OTHER PUBLICATIONS

Written Opinion for PCT/JP2020/020727 dated Aug. 25, 2020 [PCT/ISA/237].

Decision to Grant a Patent dated Dec. 15, 2020 in Japanese Application No. 2019-146416.

Extended European Search Report dated Jul. 19, 2022 in European Application No. 20849812.1.

Yue Liu et al., "Carbon Fiber Reinforced Polymer for Cable Structures—A Review", Polymers, 2015, vol. 7, pp. 2078-2099 (22 pages total).

E.Z. Li, "Research on Tribological Behavior of PEEK and Glass Fiber Reinforced PEEK Composite", Physics Procedia, 2013, vol. 50, pp. 453-460 (8 pages total).

* cited by examiner

HIGH-FREQUENCY FORCEPS

CROSS REFERENCE TO RELATED APPLICATIONS

This application claims priority to Japanese Patent Application No. 2019-146416 filed on Aug. 8, 2019, and International Patent Application No. PCT/JP2020/020727, filed on May 26, 2020, which are incorporated herein by reference in their entirety.

BACKGROUND OF INVENTION

1. Field

The present invention relates to high-frequency forceps for medical use.

2. Description of Related Art

High-frequency forceps including an insulated shaft in which a wire for moving forceps at will and a power supply cable for applying high-frequency current to the forceps are contained have been devised (refer to Patent Literature 1, for example).

Related Art List

Patent Literature 1: JP 2018-099401 A

A shaft that contains not only a wire for moving forceps but also a cable for power supply is, however, increased in diameter. If it is attempted to reduce the diameter of a shaft, the internal space thereof becomes smaller and cannot contain necessary components. In contrast, if it is attempted to reduce the outer diameter of a shaft without changing the internal space thereof, the wall thickness of the shaft needs to be reduced, which would result in insufficient strength of the shaft when the shaft is made of an insulating material of the related art.

SUMMARY OF INVENTION

The present invention has been made in view of the aforementioned circumstances, and an exemplary object thereof is to provide a new technology for reducing the thickness of a cylindrical part of forceps while satisfying desired strength and insulation thereof.

To solve the aforementioned problems, high-frequency forceps according to an aspect of the present invention are high-frequency forceps for medical use, including: a manipulation part including a grasping portion that is conductive; a cylindrical part that is inflexible, through which a wire for manipulation of the grasping portion and a cable for supplying current to the grasping portion are guided; and an insulating part that electrically insulates the manipulation part from the cylindrical part. The cylindrical part includes: an outer layer made of an insulating material; an inner layer made of an insulating material; and an intermediate layer located between the outer layer and the inner layer, and having a lower insulation resistance and a higher stiffness than the outer layer and the inner layer.

DETAILED DESCRIPTION

Figure 1:
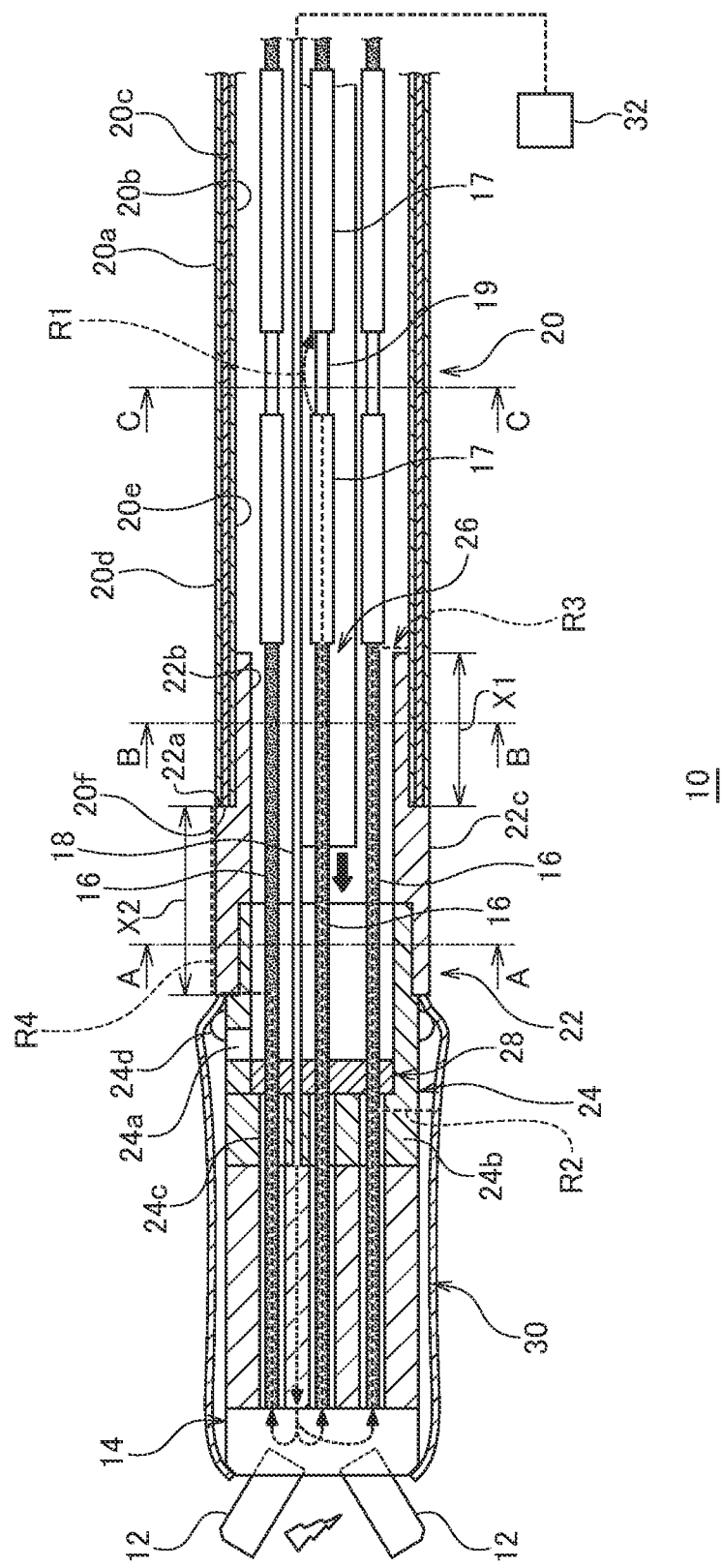
FIG. 1 is a cross-sectional view illustrating an outline structure of high-frequency forceps according to an embodiment.

The present invention will now be described on the basis of an embodiment with reference to the drawings. Components, members, and processes that are the same as or equivalent to each other illustrated in the drawings are represented by the same reference numerals, and redundant explanation will not be repeated where appropriate. The embodiment is not to limit the invention, but is an example, and any feature or any combination of features described in the embodiment is not necessarily essential to the invention.

To solve the aforementioned problems, high-frequency forceps according to an aspect of the present invention are high-frequency forceps medical use, including: a manipulation part including a grasping portion that is conductive; a cylindrical part that is inflexible, through which a wire for manipulation of the grasping portion and a cable for supplying current to the grasping portion are guided; and an insulating part that electrically insulates the manipulation part from the cylindrical part. The cylindrical part includes: an outer layer made of an insulating material; an inner layer made of an insulating material; and an intermediate layer located between the outer and the inner layer, and having a lower insulation resistance and a higher stiffness than the outer layer and the inner layer.

According to this aspect, because the outer layer and the inner layer of the cylindrical part are made of an insulating material, leakage of current through the outer circumferential surface and the inner circumferential surface of the cylindrical part is prevented. In addition, as compared with the thickness of the cylindrical part necessary for obtaining a desired strength in a case where the entire cylindrical part is made only of the same insulating material as that of the outer layer or the inner layer, the thickness of the cylindrical part can be made smaller and the outer diameter of the cylindrical part can thus be made smaller because the cylindrical part includes the intermediate layer having a higher stiffness than the outer layer and the inner layer.

The insulating part may include a flange covering an end face of the cylindrical part, and a protruding portion protruding from a center of the flange in such a manner as to cover the inner layer of the cylindrical part. As a result, even with the intermediate layer being exposed to the end face of the cylindrical part, current supplied to the grasping portions is less likely to leak to the intermediate layer via the wires. In addition, the presence of the protruding portion allows a creepage distance from the wires to the intermediate layer at the end face of the cylindrical part to be long, and prevents leakage of current from the wires to the intermediate layer.

The protruding portion may have a protruding height of 4 to 10 mm from the flange. This enables more reliable prevention of leakage of current from the wires to the intermediate layer.

the insulating part may be a cylindrical member, and have an outer circumferential surface with a length of 4 to 12 mm in an axial direction. This allows a creepage distance from the manipulation part to the intermediate layer of the cylindrical part to be long, and makes current supplied to the grasping portions less likely to leak to the intermediate layer.

The outer layer and the inner layer may be made of glass fiber reinforced plastic, and the intermediate layer may be made of carbon fiber reinforced plastic. This enables the cylindrical part to have both insulation and strength, and to be reduced in weight and diameter.

In the cylindrical part, the outer layer may have an outer diameter of 5.2 to 6 mm, the inner layer may have an inner diameter of 4 to 4.8 mm, and a total thickness of the outer layer, the intermediate layer, and the inner layer may be 0.2 to 1.0 mm. This enables the cylindrical part to have an inner diameter sufficient to guide the wires and the cable and to have an outer diameter smaller than the diameter that ensures a required strength in the related art, which reduces physical strain on a patient during surgery.

A power feeder to which current to be supplied to the grasping portion is input may further be included. The grasping portion may constitute a monopolar electrode, and a voltage of 2 to 4 kV may be applied to the power feeder. Thus, sufficient insulation is achieved in the high-frequency forceps including monopolar grasping portion to which relatively high voltage is applied.

Note that any combination of the components described above, and any expression in the present invention converted to that for a method, a device, a system, and the like also remain as aspects of the present invention.

According to the present invention, the cylindrical part of the forceps can be reduced in diameter while satisfying desired strength and insulation.

High-Frequency Forceps

High-frequency forceps are used for cutting and coagulating body tissue during surgery by grasping a subject by a pair of forceps having an electrode, and applying high-frequency current to the electrode to focus the current to the grasped site. Because current is applied to the forceps themselves, insulation of individual parts is obviously important. In addition, in a case where high-frequency forceps are repeatedly used, a structure for washability thereof also needs to be considered. Moreover, in a case where forceps are used in a state in which the forceps are inserted into a patient's abdomen, it is necessary to inflate the patient's abdomen to secure an enough surgical field. Thus, a path for introducing external carbon dioxide into the abdomen needs to be formed somewhere in the high-frequency forceps, and sealing properties to prevent leakage of carbon dioxide during surgery is also required of the high-frequency forceps. Hereinafter, an outline structure of high-frequency forceps according to the present embodiment will be described.

Figure 2A:
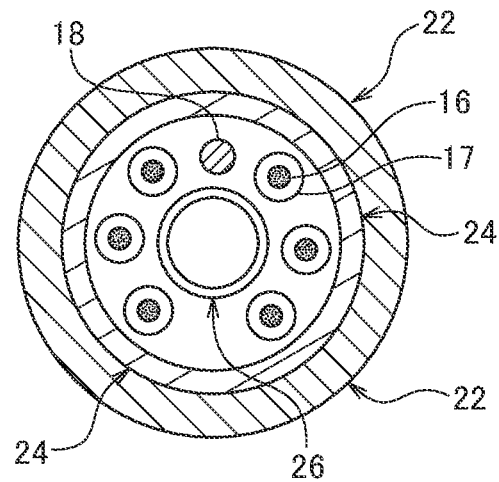
FIG. 2A is a cross-sectional view along A-A in FIG. 1.
Figure 2B:
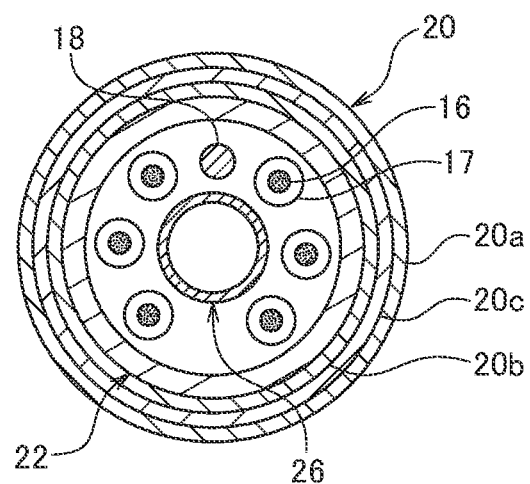
FIG. 2B is a cross-sectional view along B-B in FIG. 1.
Figure 2C:
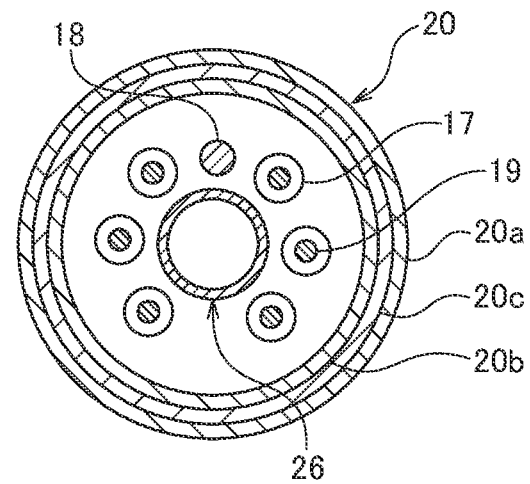
FIG. 2C is a cross-sectional view along C-C in FIG. 1.

FIG. 1 is a cross-sectional view illustrating an outline structure of the high-frequency forceps according to the present embodiment. FIG. 2A is a cross-sectional view along A-A in FIG. 1, FIG. 2B is a cross-sectional view along B-B in FIG. 1, and FIG. 2C is a cross-sectional view along C-C in FIG. 1.

As described above, high-frequency forceps 10 illustrated in FIG. 1 are for medical use, and include a manipulation part 14 having a cylindrical shape and including two grasping portions 12 that are conductive, a cylindrical part 20 that is inflexible, through which a plurality of wires 16 for manipulation of the grasping portions 12 and a cable 18 for supplying current to the grasping portions 12 are guided, and an insulating part 22 having a cylindrical shape, which electrically insulates the manipulation part 14 from the cylindrical part 20.

Part of the manipulation part 14 functions as a flexible joint in which the movements of the individual wires 16 enables the grasping portions 12 to open, close, and bend. Because the mechanistic structure inside the manipulation part 14 is not an essential feature of the present invention, illustration and explanation thereof are omitted herein. In the manipulation part 14, the cable 18 is connected with the flexible joint, and leading ends of the grasping portions 12 thus serve as an electrode. Note that the cable 18 is a conducting wire made of copper and coated with an insulating layer.

A metallic shaft 17 is connected with a back end of each of the wires 16 made of metal connected with the manipulation part 14, and the metallic shaft 17 is connected with a metallic shaft 17 with a polyarylate fiber 19 therebetween. The polyarylate fiber is an insulating material that is not easily broken when being pulled, and is excellent in low moisture absorption, dimensional stability, wear resistance, chemical resistance, and the like. This prevents leakage of current from a metallic shaft 17 to another metallic shaft 17 adjacent thereto (an insulated path R1 in FIG. 1).

A cylindrical cap 24 made of metal is disposed between the manipulation part 14 and the insulating part 22. An outlet 24a is formed in a part of a circumferential surface of the cylindrical cap 24. A cleaning solution discharged from a flush tube 26 located in the cylindrical part 20 is let out through the outlet 24a.

A disc-shaped end portion 24b of the cylindrical cap 24 has a plurality of through holes 24c through which the wires 16 and the cable 18 extend. A sealing member 28 for sealing made of silicone is placed in the cylindrical cap 24 to prevent entry of liquid through clearances in the through holes 24c into the manipulation part 14.

In addition, a projection 24d for catching a rubber cover 30 for insulation is formed on an outer circumferential surface of the cylindrical cap 24, and the insulating rubber cover 30 covering from the leading end of the manipulation part 14 to the projection 24d of the cylindrical cap 24 prevents entry of patient's body fluid or the like into the high-frequency forceps 10 through the outlet 24a during surgery. The rubber cover 30 also covers metallic parts from the leading end of the manipulation part 14 to the back end of the cylindrical cap 24, which insulates the metallic parts from the outside (an insulated path R2 in FIG. 1).

In the high-frequency forceps 10 according to the present embodiment, because current is supplied to the grasping portions 12 at the leading end of the manipulation part 14 via the cable 18, the current may partially flow toward the back end of the high-frequency forceps 10 via the wires 16. Because a controller, actuators, and various sensors for controlling the high-frequency forceps 10 are present on the back end side of the high-frequency forceps 10, propagation of high-frequency and high-voltage current to the back end side may cause noise and leakage current that affect a control system including the high-frequency forceps. The present inventor has therefore figured out various paths through which current is likely to propagate, and devised various structures for achieving sufficient insulation on the paths.

The cylindrical part 20 according to the present embodiment includes an outer layer 20a made of an insulating material, an inner layer 20b made of an insulating material, and an intermediate layer 20c located between the outer layer 20a and the inner layer 20b and having a lower insulation resistance and a higher stiffness than the outer layer 20a and the inner layer 20b.

Because the outer layer 20a and the inner layer 20b of the cylindrical part 20 are made of insulating materials as described above, leakage of current through an outer circumferential surface 20d and an inner circumferential surface 20e of the cylindrical part 20 is prevented. In addition, as compared with the thickness of the cylindrical part 20 necessary for obtaining a desired strength in a case where the entire cylindrical part 20 is made only of the same insulating material as that of the outer layer 20a or the inner layer 20b, the thickness of the cylindrical part 20 can be made smaller and the outer diameter of the cylindrical part 20 can thus be made smaller when the cylindrical part 20 includes the intermediate layer 20c having a higher stiffness than the outer layer 20a and the inner layer 20b.

The outer layer 20a and the inner layer 20b according to the present embodiment are made of glass fiber reinforced plastic. In addition, the intermediate layer 20c is made of carbon fiber reinforced plastic. The carbon fiber reinforced plastic is a material having a very high strength and a high stiffness, and thus contributes to increasing the strength of the cylindrical part 20. While, however, the carbon fiber reinforced plastic of the intermediate layer 20c is a substance that conducts electricity relatively well, the intermediate layer 20c is sandwiched by the outer layer 20a and the inner layer 20b made of glass fiber reinforced plastic, which is an insulator. This enables the cylindrical part 20 to have both insulation and strength, and to be reduced in weight and diameter.

The outer layer 20a may have an outer diameter of 5.2 to 6 mm, and the inner layer 20b may have an inner diameter of 4 to 4.8 mm. In addition, the total thickness of the outer layer 20a, the intermediate layer 20c, and the inner layer 20b may be 0.2 to 1.0 mm. This enables the cylindrical part 20 to have an inner diameter sufficient to guide the wires 16 and the cable 18 and to have an outer diameter smaller than the diameter that ensures a required strength in the related art, which reduces physical strain on a patient during surgery.

Next, the insulating part 22 constituted by a cylindrical resin cap will be described. The insulating part 22 includes a flange 22a that covers an end face 20f of the cylindrical part 20, and a protruding portion 22b that protrudes from the center of the flange 22a in such a manner as to cover the inner layer 20b of the cylindrical part 20. As a result, even with the intermediate layer 20c having a relatively low insulation resistance being exposed to the end face 20f of the cylindrical part 20, current supplied to the grasping portions 12 is less likely to leak to the intermediate layer 20c via the wires 16. In addition, the presence of the protruding portion 22b allows a creepage distance X1 from the wires 16 to the intermediate layer 20c at the end face 20f of the cylindrical part 20 to be long, and prevents leakage of current from the wires 16 to the intermediate layer 20c (see an insulated path R3 in FIG. 1).

The protruding portion 22b according to the present embodiment may have a protruding height from the flange 22a (corresponding to the creepage distance X1) of 4 to 10 mm. This enables more reliable prevention of leakage of current from the wires 16 to the intermediate layer 20c.

The insulating part 22 has an outer circumferential surface 22c from an outer edge of the flange 22a toward the cylindrical cab 24. The length X2 of the outer circumferential surface 22c in the axial direction may be 4 to 12 mm. This allows the creepage distance X2 from the manipulation part 14 to the intermediate layer 20c of the cylindrical part 20 to be long, and makes current supplied to the grasping portions 12 less likely to leak to the intermediate layer 20c (see an insulated path R4 in FIG. 1).

The cylindrical part 20 is fitted around the protruding portion 22b, and sealed and fixed by an adhesive. In addition, the cylindrical cap 24 is fitted in a leading end portion of the insulating part 22, and sealed and fixed by an adhesive.

Note that the high-frequency forceps 10 according to the present embodiment further include a power feeder 32 to which current to be supplied to the grasping portions 12 is input. The grasping portions 12 constitute a monopolar electrode, and a voltage of 2 to 4 kV at a frequency of 300 kHz to 5 MHz is applied to the power feeder 32. Thus, sufficient insulation is achieved in the high-frequency forceps 10 including monopolar grasping portions 12 to which relatively high voltage is applied.

While the present invention has been described above with reference to the embodiment, the present invention is not limited to the embodiment, and any combination or substitution of components in the embodiment as appropriate is included in the present invention. In addition, modification such as combinations, changes in the order of processes, and various changes in design in the embodiment can be made on the embodiment on the basis of knowledge of a person skilled in the art, and such modified embodiments can be within the scope of the present invention.

What is claimed is:

1. A high-frequency forceps for medical use, the high-frequency forceps comprising:
    a manipulation part including a grasping portion that is conductive;
    a cylindrical part that is inflexible, a wire for manipulation of the grasping portion and a cable for supplying current to the grasping portion being guided through the cylindrical part; and
    an insulating part that electrically insulates the manipulation part from the cylindrical part,
    wherein the cylindrical part includes:
        an outer layer made of an insulating material;
        an inner layer made of an insulating material; and
        an intermediate layer located between the outer layer and the inner layer, and having a lower insulation resistance and a higher stiffness than the outer layer and the inner layer,
    wherein the intermediate layer is exposed to an end face of the cylindrical part located nearest to the insulating part, and
    wherein the end face of the cylindrical part is exposed to the insulating part.

2. The high-frequency forceps according to claim 1, wherein the insulating part includes a flange covering the end face of the cylindrical part, and a protruding portion protruding from a center of the flange in such a manner as to cover the inner layer of the cylindrical part.

3. The high-frequency forceps according to claim 2, wherein the protruding portion has a protruding height of 4 to 10 mm from the flange.

4. The high-frequency forceps according to claim 1, wherein the insulating part is a cylindrical member, and has an outer circumferential surface with a length of 4 to 12 mm in an axial direction.

5. The high-frequency forceps according to claim 1, wherein:
    the outer layer and the inner layer are made of glass fiber reinforced plastic, and
    the intermediate layer is made of carbon fiber reinforced plastic.

6. The high-frequency forceps according to claim 5, wherein in the cylindrical part, the outer layer has an outer diameter of 5.2 to 6 mm, the inner layer has an inner diameter of 4 to 4.8 mm, and a total thickness of the outer layer, the intermediate layer, and the inner layer is 0.2 to 1.0 mm.

7. The high-frequency forceps according to claim 1, further comprising:
a power feeder to which current to be supplied to the grasping portion is input,
wherein the grasping portion constitutes a monopolar electrode, and
wherein the power feeder is configured to apply a voltage of 2 to 4 kV.

8. A high-frequency forceps comprising:
a manipulation part including a grasping portion at a leading end;
a cylindrical part provided at a distal end of the manipulation part;
an insulation part between the manipulation part and the cylindrical part configured to insulate the manipulation part from the cylindrical part;
a plurality of wires and a cable extending through an inside of the cylindrical part through to the manipulation part;
a cylindrical cap provided between the manipulation part and the insulation part; and
a rubber cover surrounding the manipulation part and the cylindrical cap, the rubber cover being configured to provide insulation and protect against external contaminants,
wherein the cylindrical part includes:
an inner layer of an insulating material;
an intermediate layer of an insulation material surrounding the inner layer; and
an outer layer of an insulating material surrounding the intermediate layer such that the intermediate layer is between the inner layer and the outer layer.

9. The high-frequency forceps according to claim 8, wherein the insulation part comprises:
a flange covering an end face of the cylindrical part; and
a protruding portion protruding from a center of the flange at the end face of the cylindrical part covering the inner layer.

10. The high-frequency forceps according to claim 8, wherein a resistance of the intermediate layer is lower than a resistance of the outer layer and the inner layer, and a stiffness of the intermediate layer is higher than a stiffness of the outer layer and the inner layer.

11. The high-frequency forceps according to claim 10, wherein the outer layer has an outer diameter of 5.2 to 6 mm, the inner layer has an inner diameter of 4 to 4.8 mm, and a total thickness of the outer layer, the intermediate layer, and the inner layer is 0.2 to 1.0 mm.

12. The high-frequency forceps according to claim 8, wherein the cylindrical cap comprises:
an outlet hole formed in a part of a circumferential surface of the cylindrical cap;
a disc-shaped end portion having a plurality of through holes configured to provide a travel path for the plurality of wires and the cable to extend from the cylindrical part to the manipulation part; and
a projection formed on an outer circumferential surface of the cylindrical cap configured to catch the rubber cover.

13. The high-frequency forceps according to claim 8, further comprising:
a metallic shaft surrounding each of the plurality of wires; and
a polyarylate fiber surrounding each of the plurality of wires, wherein
the polyarylate fiber is interposed into the metallic shaft along a length of the plurality of wires.

14. A high-frequency forceps comprising:
a manipulation part of cylindrical shape including a grasping portion at a leading end;
an insulating part of cylindrical shape connected to the trailing end of the manipulation part;
a cylindrical part connected to an end of the insulating part opposite of the manipulation part;
a plurality of wires extending from the manipulation part towards an end of the cylindrical part opposite the insulating part, the plurality of wires being arranged in a circle concentric with the manipulation part; and
a cable extending from the trailing end of the manipulation part to the cylindrical part, the cable being arranged on the circle with the plurality of wires, wherein
the insulating part and the cylindrical part coaxially surround the plurality of wires,
the cylindrical part includes
an inner layer of an insulating material coaxially surrounding the plurality of wires;
an intermediate layer of an insulation material coaxially surrounding the inner layer; and
an outer layer of an insulating material coaxially surrounding the intermediate layer, and
the intermediate layer is exposed to the end of the insulating part opposite of the manipulation part.

15. The high-frequency forceps according to claim 14, further comprising:
a metallic shaft coaxially surrounding each of the plurality of wires; and
a polyarylate fiber coaxially surrounding each of the plurality of wires, wherein
the polyarylate fiber is interposed into the metallic shaft along a length of the plurality of wires.

* * * * *